United States Patent [19]

Chauvin et al.

[11] Patent Number: 5,292,979
[45] Date of Patent: Mar. 8, 1994

[54] METHOD FOR CONVERTING ETHYLENE INTO LIGHT ALPHA OLEFINS

[75] Inventors: Yves Chauvin, Le Pecq; Dominique Commereuc, Meudon; Alain Forestiere; Francois Hugues, both of Vernaison; Lucien Saussine, Croissy sur Seine, all of France

[73] Assignee: Institut Francais Du Petrole, Rueil Malmaison, France

[21] Appl. No.: 930,596

[22] PCT Filed: Nov. 27, 1991

[86] PCT No.: PCT/FR91/00945
§ 371 Date: Oct. 2, 1992
§ 102(e) Date: Oct. 2, 1992

[87] PCT Pub. No.: WO92/10446
PCT Pub. Date: Jun. 25, 1992

[30] Foreign Application Priority Data
Dec. 4, 1990 [FR] France .................. 90 15268

[51] Int. Cl.⁵ .................. C07C 2/02
[52] U.S. Cl. .................. 585/523; 585/521; 585/530; 585/532

[58] Field of Search .......... 585/517, 523, 524, 525, 585/528, 530, 521, 532

[56] References Cited

U.S. PATENT DOCUMENTS

3,879,485 4/1975 Belov et al.
4,434,312 2/1984 Langer, Jr. .................. 585/523

FOREIGN PATENT DOCUMENTS

0114416 8/1984 European Pat. Off.
2318953 11/1973 Fed. Rep. of Germany.
2243173 4/1975 France.

*Primary Examiner*—Patrick P. Garvin
*Assistant Examiner*—Brent M. Peebles
*Attorney, Agent, or Firm*—Millen, White, Zelano & Branigan

[57] ABSTRACT

Process for the conversion of ethylene into light alpha olefins, mainly 1-butene, 1-hexene and 1-octene, in which the ethylene is contacted with a catalyst obtained by reacting a performed mixture of alkyl zirconate and ether with a chlorine or bromine-containing aluminum compound.

21 Claims, No Drawings

METHOD FOR CONVERTING ETHYLENE INTO LIGHT ALPHA OLEFINS

SUMMARY OF THE INVENTION

The present invention relates to a process for the oligomerization of ethylene into light alpha olefins, mainly into 1-butene, 1-hexene and 1-octene.

In U.S. Pat. No. 2,943,125, K. Ziegler describes a method for the dimerization of ethylene into 1-butene by means of a catalyst obtained by mixing trialkyl aluminum and a zirconium or titanium tetraalkoxide. During the reaction, there is also formed a certain quantity of polyethylene having a high molecular weight and which is significantly prejudicial. Several improvements have been proposed for reducing the polymer quantity, particularly in U.S. Pat. No. 3,686,350, which recommends the use of organic phorphorous compounds, together with elements of the catalyst, U.S. Pat. No. 4,101,600, which describes the treatment of the catalyst by hydrogen, and U.S. Pat. No. 3,879,485, which claims the use of various ethers as solvents for the reaction medium.

The oligomerization of ethylene into alpha olefins having various molecular weights has been known since 1960 to 1965. Besides methods involving a stoichiometric chain growth reaction, e.g., using an organoalumina compound, several catalytic methods have been discovered, which use various metals such as titanium, zirconium, chromium, nickel or rare earths and which are mainly used in Ziegler-type formulations. All these methods give mixtures of oligomers having a carbon number which varies widely and which is between 4 and 30, or may even exceed 30. These mixtures are suitable for uses which had previously been reserved for these oligomers (particularly detergents and plasticizers).

For some years now there has been an increasing demand for lower oligomers, mainly 1-butene, 1-hexene and 1-octene, which are used as comonomers with ethylene in the production of low linear density polyethylenes.

According to the invention, it has now been found that the catalysts obtained by mixing at least one particular aluminum compound with at least one performed mixture of at least one ether and at least one alkyl zirconate have an unexpected selectivity for the formation of lower oligomers, mainly 1-butene, 1-hexene and 1-octene.

The invention therefore relates to an improved process for converting ethylene into light alpha olefins, in which the ethylene is contacted with at least one catalyst obtained by reacting a performed mixture of alkyl zirconate and ether, in an ether/zirconate molar ratio of 0.5:1 to 10:1, with at least one aluminum compound of general formula $AlR_nX_{3-n}$, in which R is a hydrocarbyl radical, X is a bromine or chlorine atom and n is a number between 1 and 2.

Therefore, the ethers are used in a molar ratio of 0.5 to 10 and preferably 1 and 4, more specifically 2 to 3 moles of ether per mole of alkyl zirconate. Without being bound by any theory, it is considered that the ether complex on the zirconium atom permitting the hexacoordination, which the zirconium otherwise only carried out by autoassociation.

The ethers used in the invention can be monoethers or polyethers. Preference is given to the use of monoethers, such as e.g., diethyl ethers, diisoamyl ether, methyl tert. butyl ether and tetrahydrofuran.

The alkyl zirconates used in the invention are generally in accordance with the general formula $Zr(OR')_4$, in which R' is a straight or branched alkyl radical preferably having 2 to 8 carbon atoms. It is possible to use tetraethyl zirconate, or tetra-2-ethyl hexyl zirconate.

The aluminum compounds used in the invention are represented by the general formula $AlR_nX_{3-n}$, in which R is a hydrocarbyl radical, preferably alkyl having 2 to 6 carbon atoms, X is a chlorine or bromine atom and preferably a chlorine atom and n is a number between 1 and 2 (n can in particular be 1 or 2). Reference is, e.g., made to chlorodiethyl aluminum dichloroethyl aluminium, ethyl aluminum sesquichloride or mixtures thereof.

The catalyst components can be contacted within a hydrocarbon, e.g., a saturated hydrocarbon, such as hexane or heptane and/or one or more oligomerization byproducts, such as decenes, dodecenes or higher oligomers.

The molar ratio between the aluminum compound and the alkyl zirconate is approximately 1:1 to 30:1 and preferably approximately 5:1 to 20:1. The zirconium concentration in the thus prepared catalytic solution is advantageously between $10^{-4}$ and 0.5 mole per liter and is preferably between $2.10^{-3}$ and 0.1 mole per liter. The preshaped mixture of alkyl zirconate and ether is normally reacted with the aluminum compound at a temperature between $-10°$ and $+50°$ C. preferably between $0°$ and $40°$ C. and, e.g., at ambient temperature ($15°$ to $25°$ C.). This reaction can be carried out under an ethylene or inert gas atmosphere.

The catalytic solution obtained in this way can be used as it is or can be diluted by adding products of the reaction.

In a special embodiment of the discontinuous catalytic oligomerization reaction, a chosen volume of the catalytic solution, prepared as described hereinbefore, is introduced into a reactor equipped with the usual stirring and cooling systems and then pressurization takes place by ethylene at a pressure generally between 0.5 and 10 MPa, preferably between 1 and 6 MPa. The temperature is generally maintained between $20°$ C. and $80°$ C., preferably between $40°$ and $75°$ C. The oligomerization reactor is supplied with ethylene at a constant pressure until the total liquid volume produced represents between 2 and 50 times the volume of the initially introduced catalytic solution. The catalyst is then destroyed, e.g., by the addition of water and the products of the reaction and the possible solvent are drawn off and separated.

In the case of continuous operation, the procedure is preferably as follows. The catalytic solution is injected at the same time as the ethylene into a reactor stirred by conventional mechanical means or by an external recirculation. The temperature is kept at between $20°$ and $80°$ C., preferably between $40°$ and $75°$ C. and the pressure must be adequate to ensure that all the compounds are in the liquid phase. As a function of the catalyst and ethylene flow rates, said pressure 0.5 and 10 MPa. Through a relief valve, which keeps the pressure constant, flows part of the reaction mixture at a mass flow rate equal to that of the fluids introduced. The thus relieved fluid is passed into a distillation column system making it possible to separate the oligomers from the ethylene on the one hand, whereby the ethylene can be fed into the reactor, and then the individual oligomers on the other. The heavy catalyst-containing products can be incinerated.

EXAMPLES

The following examples illustrate the invention without limiting its scope.

EXAMPLE 1

Into a stainless steel autoclave with a volume of 250 ml and provided with a double envelope making it possible to regulate the temperature by water circulation is introduced successively under an argon atmosphere and at ambient temperature 0.79 mole (i.e., $0.79 \cdot 10^{-3}$ mole) of tetra-n-butyl zirconate $Zr(OBu)_4$ and 1.58 mmole of tetrahydrofuran dissolved in 50 ml of n-heptane and then 4.40 mmoles of ethyl aluminum sesquichloride also dissolved in 50 ml of n-heptane.

After reacting for a few minutes, the temperature is raised to 60° C., while introducing into the autoclave ethylene at a constant pressure of 4 MPa (the pressure is maintained at this value by complementary ethylene introduction as the ethylene is consumed). After reacting for 60 minutes, ethylene introduction is stopped and the catalyst destroyed by the injection under pressure of 2 ml of water. In all, 70 g of ethylene have been consumed.

The composition of the products obtained is given in Table 1. In addition, 0.55% by weight of solid polymer, based on the consumed ethylene, is collected.

EXAMPLE 2

Using the same equipment as in example 1 and under the same conditions, except that twice the quantity of tetrahydrofuran is introduced, 35.7 g of ethylene were consumed during the reaction, which was stopped after 170 minutes.

The composition of the products obtained is given in Table 1. In addition, 3.8% by weight of solid polymer, based on the consumed ethylene, were collected.

EXAMPLE 3

Using the same equipment as in example 1, the following were successively introduced under an argon atmosphere and at ambient temperature: 0.19 mmole of $Zr(OBu)_4$ and 0.39 mmole of tetrahydrofuran dissolved in 10 ml of n-heptane and then 1.06 mmole of ethyl aluminum sesquichloride dissolved in 15 ml of n-heptane.

After reacting for a few minutes the temperature was raised to 70° C., while introducing into the autoclave ethylene at a constant pressure of 4 MPa. After reacting for 180 minutes ethylene introduction was stopped and the catalyst destroyed by the injection under pressure of 2 ml of water. In all, 61.6 g of ethylene were consumed.

The composition of the products obtained is given in Table 1. In addition, 1.2% by weight of solid polymer, based on the ethylene consumed, were collected.

EXAMPLE 4

Into the same equipment as in example 1 were successively introduced under an ethylene atmosphere and at ambient temperature: 0.39 mmole of $Zr(OBu)_4$ and 0.79 mmole of tetrahydrofuran dissolved in 50 ml of n-heptane, followed by 2.17 mmoles of ethyl aluminum sesquichloride also dissolved in 50 ml of n-heptane.

After reacting for a few minutes the temperature is raised to 75° C. and the ethylene pressure is adjusted to 4 MPa. After reacting for 55 minutes, ethylene introduction is stopped and the catalyst destroyed by injecting under pressure 2 ml of water. In all, 77 g of ethylene were consumed in 55 minutes.

The composition of the products obtained is given in Table 1. In addition, 0.69% by weight of solid polymer, based on the ethylene consumed, was collected.

EXAMPLE 5 (comparative)

Using the same equipment as in example 4 and under the same conditions, except that there was no tetrahydrofuran introduction, 71.6 g of ethylene were consumed in 100 minutes of reaction.

The composition of the products obtained is given in Table 1. In addition, 4.6% by weight of solid polymer, based on the ethylene consumed, were collected.

This example clearly demonstrates that the prior art procedure used therein gives less satisfactory results than those obtained in the examples according to the invention and in particular an unfavorable distribution of products for the light alpha olefins $C_4$, $C_6$ and $C_8$.

EXAMPLE 6

Into the same equipment as example 1 were successively introduced under an argon atmosphere and at ambient temperature 0.38 mmole of $Zr(OBu)_4$ and 0.76 mmole of tetrahydrofuran dissolved in 10 ml of n-heptane, followed by a mixture of 1.14 mmole of $AlEt_3$ and 3.42 mmole of $AlEtCl_2$ (this mixture is equivalent to 2.28 mmole of ethyl aluminum sesquichloride) dissolved in 15 ml of n-heptane.

After reacting for a few minutes the temperature was raised to 60° C., whilst introducing into the autoclave ethylene at a constant pressure of 4 MPa. After reacting for 270 minutes, ethylene introduction was stopped and the catalyst destroyed by the injection under pressure of 2 ml of water. In all, 106 g of ethylene were consumed.

The composition of the products obtained is given in Table 1. In addition, 1.2% by weight of solid polymer, based on the ethylene consumed, were collected.

EXAMPLE 7

Into a stainless steel autoclave with a volume of 1 liter and provided with a double envelope making it possible to regulate the temperature by the circulation of water were successively introduced under a nitrogen atmosphere and at ambient pressure 0.78 mmole of $Zr(OBu)_4$ and 1.53 mmole of tetrahydrofuran dissolved in 100 ml of n-heptane, then 4.68 mmoles of ethyl aluminum sesquichloride also dissolved in 100 ml of n-heptane.

After reacting for a few minutes, the temperature was raised to 50° C., while introducing into the autoclave ethylene at a constant pressure of 4 MPa.

After 210 minutes reaction, ethylene introduction was stopped and the catalyst destroyed by the injection under pressure of 5 ml of water. In all, 195 g of ethylene were consumed.

The composition of the products obtained is given in Table 1. In addition, collection took place of 0.31% by weight of solid polymer based on the ethylene consumed.

TABLE 1

| Example | Distribution of products obtained (% by weight) | | | | Content of alpha olefins obtained (% by weight) | | |
|---|---|---|---|---|---|---|---|
| | $C_4$ | $C_6$ | $C_8$ | $C_{10}^+$ | in $C_4$ | in $C_6$ | in $C_8$ |
| 1 | 30.0 | 27.0 | 15.9 | 27.1 | 97.1 | 91.0 | 91.2 |
| 2 | 42.4 | 22.8 | 9.9 | 24.9 | 97.1 | 92.1 | — |
| 3 | 30.6 | 32.6 | 19.2 | 17.6 | 98.2 | 87.3 | 92.2 |

TABLE 1-continued

| Example | Distribution of products obtained (% by weight) | | | | Content of alpha olefins obtained (% by weight) | | |
|---|---|---|---|---|---|---|---|
| | $C_4$ | $C_6$ | $C_8$ | $C_{10}^+$ | in $C_4$ | in $C_6$ | in $C_8$ |
| 4 | 26.1 | 27.7 | 18.7 | 27.5 | 97.7 | 90.6 | 95.4 |
| 5 | 16.9 | 17.7 | 28.3 | 37.1 | 94.4 | 83.0 | — |
| 6 | 38.1 | 35.4 | 17.4 | 9.1 | 96.0 | 91.9 | 92.1 |
| 7 | 32.6 | 27.9 | 18.0 | 21.5 | 97.0 | 95.0 | — |

(with $C_4$ = butenes, $C_6$ = hexenes, $C_8$ = octenes, $C_{10}^+$ = decenes and higher olefins).

We claim:

1. A process for conversion of ethylene into light alpha olefins comprising contacting ethylene with at least one catalyst obtained by the reaction of a performed mixture of alkyl zirconate and ether, in an ether/zirconate molar ratio of 0.5:1 to 10:1, with at least one aluminum compound of general formula $AlR_nX_{3-n}$, in which R is a hydrocarbyl radical, X is a chlorine or bromine atom and n is 1-2.

2. A process according to claim 1, wherein said ether/zirconate molar ratio is between 1:1 to 4:1.

3. A process according to claim 1, wherein said reaction is performed in a hydrocarbon.

4. A process according to claim 1, wherein said ether is diethyl ether, diisoamyl ether, methyl tert. butyl ether or tetrahydrofuran.

5. A process according to claim 4, wherein said ether is tetrahydrofuran.

6. A process according to claim 1, wherein said alkyl zirconate is tetra-n-propyl zirconate or tetra-n-butyl zirconate.

7. A process according to claim 1, wherein said aluminum compound is ethyl aluminum sesquichloride.

8. A process according to claim 1, wherein the molar ratio between the aluminum compound and the alkyl zirconate is 1:1 to 30:1 and the zirconium concentration is between $10^{-4}$ and 0.5 mole per liter.

9. A process according to claim 1, wherein said reaction is performed at a temperature between 0° and +40° C. and under an ethylene or inert gas atmosphere.

10. A process according to claim 1, wherein the conversion of ethylene into light alpha olefins takes place at a temperature between +40° to +75° C. and under a pressure between 1 and 6 MPa.

11. A process according to claim 4, wherein said alkyl zirconate is tetra-n-propylzirconate or tetra-n-butyl zirconate.

12. A process according to claim 11, wherein said ether/zirconate molar ratio is between 1:1-4:1.

13. A process according to claim 11, wherein said aluminum compound is ethyl aluminum sesquichloride.

14. A process according to claim 13, wherein the molar ratio between the aluminum compound and the alkyl zirconate is approximately 1:1 to 30:1 and the zirconium concentration is between $10^{-4}$ and 0.5 molar per liter.

15. A process according to claim 11, wherein said ether is tetrahydrofuran.

16. A process according to claim 12, wherein said ether is tetrahydrofuran.

17. A process according to claim 13, wherein said ether is tetrahydrofuran.

18. A process according to claim 14, wherein said ether is tetrahydrofuran.

19. A process according to claim 12, wherein said aluminum compound is ethyl aluminum sesquichloride.

20. A process according to claim 17, wherein said alkyl zirconate is tetra-n-butyl zirconate.

21. A process according to claim 1, wherein R is $C_{2-4}$-alkyl and said alkyl zirconate is of the formula $Zr(OR')_4$ wherein R' is $C_{2-8}$-alkyl.

* * * * *